United States Patent
Miyano et al.

[11] Patent Number: 6,040,465
[45] Date of Patent: Mar. 21, 2000

[54] PROCESS FOR PRODUCING OPTICALLY ACTIVE β-LACTONES

[75] Inventors: Sotaro Miyano; Tetsutaro Hattori, both of Sendai; Osamu Uesugi, Yokohama; Yasufumi Tamai, Sendai; Noboru Sayo, Hiratsuka, all of Japan

[73] Assignee: Takasago International Corporation, Tokyo, Japan

[21] Appl. No.: 09/265,371

[22] Filed: Mar. 10, 1999

[30] Foreign Application Priority Data

Mar. 11, 1998 [JP] Japan .................................. 10-101674

[51] Int. Cl.[7] ........................... C07D 305/12; B01J 20/00
[52] U.S. Cl. ............................................. 549/510; 502/414
[58] Field of Search ............................................. 549/510

[56] References Cited

PUBLICATIONS

Asymmetric (2+2) cycloaddition of ketene . . . Yasufumi Tamai et al J. Chem. Soc. 1994, pp. 2281–2282, Jul. 12, 1994.

*Primary Examiner*—Alan L. Rotman
*Assistant Examiner*—Rita Desai
*Attorney, Agent, or Firm*—Kubovcik & Kubovcik

[57] ABSTRACT

Disclosed is a process for producing an optically active β-lactone represented by the general formula (I):

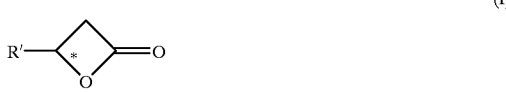

wherein $R^1$ represents an alkyl group having 1–9 carbon atoms which can be branched or a cycloalkyl group having 5–7 carbon atoms. The process comprises reacting an aldehyde represented by the general formula (II):

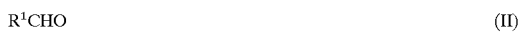

$$R^1CHO \qquad (II)$$

wherein $R^1$ is the same as defined above, with a ketene represented by the general formula (III):

$$CH_2{=}C{=}O \qquad (III)$$

in the presence of a bissulfonamide/aluminum complex represented by the general formula (IV):

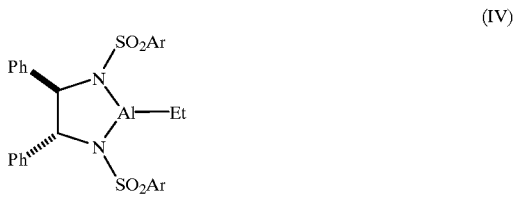

wherein Ar represents 2,4,6-$(R^2)_3C_6H_2$ (wherein $R^2$ represents an alkyl group having 2–4 carbon atoms), Et represents an ethyl group and Ph represents a phenyl group.

2 Claims, No Drawings

PROCESS FOR PRODUCING OPTICALLY ACTIVE β-LACTONES

BACKGROUND OF THE INVENTION

1. Field of the Invention

This invention relates to a process for producing optically active β-lactones useful as starting materials for polymers or pharmaceuticals, or as intermediates of liquid crystals.

2. Description of Prior Art

An optically active β-lactone has been prepared by a [2+2] addition reaction conventionally between an aldehyde and a ketene. Examples of processes for producing the optically active β-lactone by a [2+2] addition reaction include (1) a process in which trichloroaldehydes or trichloroketones are reacted with ketenes in the presence of a catalytic amount of quinines or quinidines (H. Wynberg et al., *J. Org. Chem.* Vol 50, pp. 1977 (1985)), (2) a process in which a trichloroaldehyde is reacted with a ketene in the presence of a polymeric cinchona alkaloid as a catalyst (C. E. Song et al., *Tetrahedron: Asymmetry*, Vol 5, pp. 1215 (1994)), (3) a process in which an aldehyde is reacted with a ketene in the presence of an optically active binaphthol/aluminum complex (Y. Tamai et al., *J. Chem. Soc. Perkin Trans.* 1, pp. 1549 (1994)), (4) a process in which an aldehyde is reacted with a ketene in the presence of an optically active bissulfonamide/aluminum complex (Y. Tamai et al., *J. Chem. Soc. Chem. Commun.*, pp. 2281 (1994)) and (5) a process in which an aldehyde is reacted with a trimethylsilylketene in the presence of an optically active bissulfonamide/aluminum complex (B. W. Dymock et al., *Chem. Commun.*, pp. 1053 (1996)).

However, in processes (1) and (2), only a specific substrate such as a trichloroaldehyde is disclosed, and in processes (3) and (4), products with a lower enantiomer excess are obtained. Moreover, in process (5) a trimethylsilylketene which is difficult to handle is used to produce β-lactones.

All the foregoing processes have drawbacks such as the use of specific substrates and insufficient enantiomer excess and hence there have been a strong demand to provide a process having none of these drawbacks.

SUMMARY OF THE INVENTION

Accordingly, an object of the present invention is to provide a process for producing an optically active β-lactone (I). The optically active β-lactone (I) is produced by reacting an aldehyde (II) with a ketene (III) in the presence of a specific bissulfonamide/aluminum complex (IV). This reaction is represented by the following reaction formula:

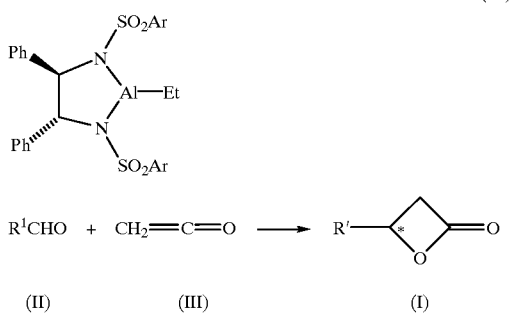

wherein $R^1$ represents an alkyl group having 1–9 carbon atoms which can be branched or a cycloalkyl group having 5–7 carbon atoms, Ar represents 2,4,6-$(R^2)_3C_6H_2$, $R^2$ represents an alkyl group having 2–4 carbon atoms, Et represents ethyl and Ph represents phenyl.

DETAILED DESCRIPTION OF THE INVENTION

In the aldehyde (II) used as the starting material of the present invention, $R^1$ is an alkyl group having 1–9 carbon atoms which can be branched or an cycloalkyl group having 5–7 carbon atoms. Specific examples of the aldehyde (II) include acetaldehyde, propyl aldehyde, n-butyl aldehyde, 2-methylpropyl aldehyde, n-valeraldehyde, 2-methylbutyl aldehyde, 3-methylbutyl aldehyde, 2,2-dimethylpropyl aldehyde, n-hexyl aldehyde, 2-methylvaleraldehyde, 3-methylvaleraldehyde, 4-methylvaleraldehyde, 2,2-dimethylbutyl aldehyde, 2,3-dimethylbutyl aldehyde, 3,3-dimethylbutyl aldehyde, n-heptylaldehyde, 2-methylhexyl aldehyde, 2-ethylvaleraldehyde, 2-propylbutyl aldehyde, 3-ethylvaleraldehyde, 3-methylhexyl aldehyde, 4-methylhexyl aldehyde, 5-methylhexyl aldehyde, 2,2-dimethylvaleraldehyde, 2,3-dimethylvaleraldehyde, 2,4-dimethylvaleraldehyde, 3,3-dimethylvaleraldehyde, 3,4-dimethylvaleraldehyde, 4,4-dimethylvaleraldehyde, 2,2,3-trimethylbutyl aldehyde, 2,3,3-trimethylbutyl aldehyde, n-octyl aldehyde, 2-methylheptylaldehyde, 3-methylheptylaldehyde, 4-methylheptylaldehyde, 5-methylheptylaldehyde, 6-methylheptylaldehyde, 2-ethylhexyl aldehyde, 3-ethylhexyl aldehyde, 4-ethylhexyl aldehyde, 2-propylvaleraldehyde, 2,2-dimnethylhexyl aldehyde, 2,3-dimethylhexyl aldehyde, 2,4-dimethylhexyl aldehyde, 2,5-dimethylhexyl aldehyde, 3,3-dimethylhexyl aldehyde, 3,4-dimethylhexyl aldehyde, 3,5-dimethylhexyl aldehyde, 4,4-dimethylhexyl aldehyde, 4,5-dimethylhexyl aldehyde, 5,5-dimethylhexyl aldehyde, n-nonyl aldehyde, cyclopentylcarbaldehyde, cyclohexylcarbaldehyde and cycloheptylcarbaldehyde.

The ketene (III) which is another starting material can be prepared according to well-known processes. More concretely, for example, it can be prepared by heating acetone according to the process described in *J. Am. Chem. Soc.*, Vol 110, pp. 1841 (1988) (W. J. Evans et al.).

A selection of the catalyst which is allowed to coexist in the reaction mixture is among the most important features of the present invention. The use of an optically active bissulfonamide/aluminum complex represented by the following formula (IV) as the catalyst brings about a more improved enantiomer excess in contrast to the conventionally known reaction processes:

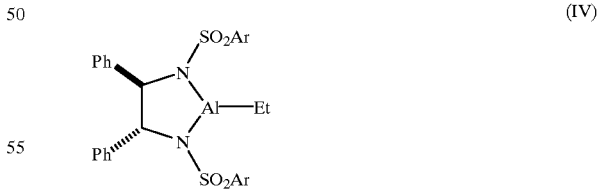

wherein Ar, Et and Ph are the same as defined above.

A bissulfonamide ligand of the bissulfonamide/aluminum complex may be synthesized, for example, according to the process described by E. J. Corey et al., in *J. Am. Chem. Soc.*, Vol 111, pp. 5493 (1989) For example, a bissulfonamide ligand having an isopropyl group as $R^2$ can be prepared with ease by reacting commercially available diphenylethylenediamine with 2,4,6-(i-Pr)$_3$C$_6$H$_2$SO$_2$Cl in the presence of a base, e.g., triethylamine.

The aluminum complex can be synthesized with ease by reacting bissulfonamide with triethylaluminum in toluene according to, for example, the method of E. J. Corey et al., *J. Am. Chem. Soc.*, Vol 114, pp. 7938 (1992).

The bissulfonamide/aluminum complex obtained in this manner and represented by the general formula (IV) is effective as a catalyst of an asymmetrically synthesis and various optically active compounds can be produced in the presence of the complex. In particular, this catalyst is of great advantage for the preparation of optically active β-lactones.

The above-mentioned bissulfonamide/aluminum complexes embrace a (1R, 2R) derivative synthesized from (1R, 2R)-diphenylethylenediamine and a (1S, 2S) derivative synthesized from (1S, 2S)-diphenylethylenediamine. These derivatives may be used so as to correspond to the absolute configuration of the optically active β-lactone, the objective product. Specifically, if a (1R, 2R) derivative of bissulfonamide/aluminum complex is used, (1R)-β-lactone is obtained whereas if a (1S, 2S) derivative of bissulfonamide/aluminum complex is used, (1S)-β-lactone is obtained.

In the present invention, the optically active β-lactone is prepared in an atmosphere of inert gas, e.g., argon or nitrogen gas, by dissolving the aldehyde (II) and the bissulfonamide/aluminum complex (IV) in an organic solvent and by introducing the ketene (III) into the mixture to react these compounds with each other.

Examples of the organic solvent used in the reaction include aromatic hydrocarbons such as benzene and toluene; halogenated hydrocarbons such as methylene chloride and chloroform; and aprotic solvents such as tetrahydrofuran and diethyl ether. Among these, aromatic hydrocarbons such as benzene and toluene or halogenated hydrocarbons such as methylene chloride and chloroform are preferable.

The amount of the aldehyde (II) to be used is generally 1 mol/L to 0.01 mol/L and preferably 0.2 mol/L to 0.02 mol/L based on the organic solvent.

It is preferable that the bissulfonamide-aluminum complex (IV) as the catalyst is used in an amount of about 1 to 20 mol % and particularly about 5 to 10 mol % based on the aldehyde (II) to obtain products with a high enantiomer excess. It is preferable that the ketene(III) is about 1 to 5 times by mol and particularly about 2 to 4 times by mol based on the aldehyde (II).

The reaction temperature is about −120 to −50° C. and preferably about −100 to −70° C. The reaction time is preferably about 1 to 10 hours.

After the reaction is finished, an acid, e.g., dilute hydrochloric acid, is added to the reaction mixture, followed by extraction using the organic solvent used in the reaction or other organic solvents such as ethyl acetate or butyl acetate. After the extract is washed, the organic layer is dried as required, followed by filtration, concentration and distillation to purify to produce the objective optically active β-lactone in a high yield.

The present invention selectively uses a specific optically active bissulfonamide/aluminum complex as the catalyst for an asymmetric [2+2] addition reaction to thereby produce an optically active β-lactone from an aldehyde and a ketene in an efficient manner and also at a high enantiomer selectivity. The present invention is thus a superior industrial process.

EXAMPLES

The invention will be explained in more detail by way of Examples which are not intended to be limiting of the present invention.

The following analysis instruments were adopted for analysis in the following examples.

$^1$H Nuclear magnetic resonance spectrum (hereinafter abbreviated as "$^1$H-NMR"): AC-250 (250 MHz), DPX-400 (manufactured by BRUKER Inc.)

IR spectrum: FTIR-8300 (manufactured by Shimadzu Corporation)

Meter measuring optical rotation: DIP-1000 (manufactured by JASCO Corporation)

Gas chromatography: GC-14A (manufactured by Shimadzu Corporation)

High performance liquid chromatography: LC-10AD, SPD-10A (manufactured by Shimadzu Corporation)

Reference Example 1

Synthesis of (1R, 2R)-1,2-N,N-bis(2,4,6-triisopropylbenzenesulfonylamino)-1,2-diphenylethane A 50 ml two-necked round-bottom flask was charged with 104 mg (0.491 mmol) of a methylene chloride solution (5 ml) of (1R, 2R)-(+)-1,2-diphenylethylenediamine, to which was added 136 mg (1.11 mmol) of 4-dimethylaminopyridine at 0° C. in flowing nitrogen gas. To the mixture further cooled to −78° C. was added 305 mg (1.01 mmol) of 2,4,6-triisopropylbenzenesulfonyl chloride synthesized according to the process described in the literature (E. H. Huntress et al., *J. Am. Che. Soc.*, Vol 62, pp. 511 (1940)). After the reaction mixture was stirred for 2 hours, 1N HCl (5 ml) was added to the reaction mixture to terminate the reaction. The resulting mixture was extracted using methylene chloride (20 ml, four times). The organic layer was washed with saturated brine and dried using $Na_2SO_4$ anhydride. The dried product was further filtered, followed by distilling the solvent and drying under reduced pressure, to obtain 380 mg of a crude product of the title compound. The crude product was purified by silica gel column chromatography (methylene chloride/hexane=1/5→1) and further by silica gel column chromatography (ethyl acetate/hexane=1/20) to obtain 318 mg (yield: 87%) of the title compound as white crystals.

$^1$H-NMR (CDCl$_3$): δ(ppm)

1.04 (d, J=6.7 Hz, 12H), 1.17 (dd, J=6.7, 6.9 Hz, 24H), 2.82 (sept, J=6.9 Hz, 2H), 3.99 (sept, J=6.7 Hz, 4H), 4.46 (br, 2H), 5.70 (br, 2H), 6.58 (d, J=7.4 Hz, 4H), 6.89 (t, J=77.4 Hz, 4H), 6.97 (t, J=7.3 Hz, 2H), 6.99 (s, 4H)

IR(KBr): cm$^{-1}$ 3445, 3315, 2965, 2870, 1596, 1559, 1453, 1419, 1377, 1356, 1311, 1251, 1150, 1103, 1057, 1037, 935, 692, 654, 559

Melting point: 87.6–89.4° C.

Elemental analysis $C_{44}H_{60}N_2O_4S_2$ Calcd.: C 70.93; H 8.12; N 3.76; S 8.61

Found: C 71.06; H 8.21; N 3.67; S 8.44

Example 1

Synthesis of (R)-4-cyclohexyloxetan-2-one

In flowing nitrogen gas, a two-necked flask was charged with 149 mg (0.2 mmol) of (1R, 2R)-1,2-N,N-bis(2,4,6-triisopropylbenzenesulfonylamino)-1,2-diphenylethane, which was then dissolved by addition of 20 ml of dry toluene. The mixture, to which 0.22 ml (0.2 mmol) of triethylaluminum (0. 91 N toluene solution) was added, was stirred at 80° C. for one hour to prepare a catalyst solution. 236 mg (2.1 mmol) of cyclohexyl aldehyde was added to the solution at −78° C. An excess of ketene gas (about 2.5 equivalents) was then blown into the mixed solution for 10 minutes. After the reaction mixture was stirred for one hour, 10 ml of 1N HCl was added to the reaction mixture to terminate the reaction. The resulting mixture was extracted with methylene chloride (30 ml, five times). The organic layer was washed with saturated brine (100 ml, one time) and dried using $Na_2SO_4$ anhydride. The dried product was filtered and the solvent was then distilled to obtain a crude product of the title compound. The crude product was quantitatively measured by gas chromatography (CROMPACK, 0.25 mm×30 m) using n-butyl benzoate as the internal standard material (yield: 99%, 85% ee). The crude product was, in turn, distilled (60° C., 0.15 mmHg) by a bulb to bulb distillation to isolate the title compound (yield: 96%, 337 mg).

$^1$H-NMR (CDCl$_3$): δ(ppm)

0.96–1.05 (2H, m), 1.19–1.32 (3H, m), 1.58–1.82 (5H, m), 1.97–2.08 (1H, m), 3.11 (1H, dd, J=16.2 4.4 Hz), 3.42 (1H, dd, J=16.2, 5.8 Hz), 4.16–4.24 (1H, m)

IR: 1821 cm$^{-1}$ (C=O)

Example 2

Synthesis of (R)-4-cyclohexyloxetan-2-one

The title compound with 85% ee was obtained in the same manner as in Example 1 except that the reaction temperature was changed to −95° C. from −78° C.

Comparative Example 1

Synthesis of (R)-4-cyclohexyloxetan-2-one

The title compound with 69% ee was obtained in the same manner as in Example 1 except that (1R, 2R)-1,2-N,N-bis (3,5-bistrifluoromethanebenzenesulfonylamino)-1,2-diphenylethane was used as the catalyst instead of (1R, 2R)-1,2-N,N-bis(2,4,6-triisopropylbenzenesulfonylamino)-1,2-diphenylethane.

Example 3 and Example 4

The same procedures as in Example 1 were conducted, except that n-hexyl aldehyde and n-nonyl aldehyde were used as the aldehyde instead of cyclohexyl aldehyde, to prepare (R)-4-n-hexyloxetan-2-one and (R)-4-n-nonyloxetan-2-one in yields of 88% and 89% with 77% ee and 78% ee, respectively.

Comparative Example 2 and Comparative Example 3

The same procedures in Examples 3 and 4 were conducted, except that (1R, 2R)-1,2-N,N-bis(3,5-bistrifluoromethanebenzenesulfonylamino)-1,2 diphenylethane was used as the catalyst instead of (1R, 2R)-1,2-N,N-bis(2,4,6-triisopropylbenzenesulfonylamino)-1,2-diphenylethane, to prepare (R)-4-n-hexyloxetan-2-one and (R)-4-n-nonyloxetan-2-one with 31% ee and 35% ee, respectively.

What is claimed is:

1. A process for producing an optically active β-lactone of formula (I):

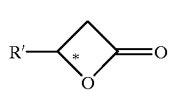

(I)

wherein $R^1$ is an alkyl group having 1–9 carbon atoms which is optionally branched or a cycloalkyl group having 5–7 carbon atoms; the process comprising reacting an aldehyde of formula (II):

(II)

wherein $R^1$ is the same as defined above, with a ketene of formula (III):

(III)

in the presence of a bissulfonamide/aluminum complex of formula (IV):

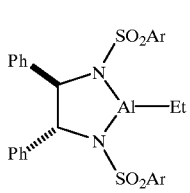

(IV)

wherein Ar is 2,4,6-$(R^2)_3C_6H_2$, wherein $R^2$ is an alkyl group having 2–4 carbon atoms, Et is an ethyl group and Ph is a phenyl group.

2. A process for producing an optically active β-lactone according to claim 1, wherein said bissulfonamide/aluminum complex is a compound of formula (V):

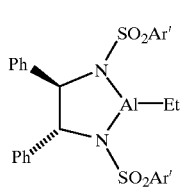

(V)

wherein Ar$^1$ is 2,4,6-(i-Pr)$_3$C$_6$H$_2$, Et is an ethyl group and Ph is a phenyl group.

* * * * *